United States Patent [19]

Stroh

[11] Patent Number: 5,075,126

[45] Date of Patent: Dec. 24, 1991

[54] USE OF A SILICONE AS A COATING FOR SURFACES OF METALLIC OBJECTS COMING INTO DIRECT CONTACT WITH THE HUMAN SKIN

[76] Inventor: Heidi Stroh, Hoyerweg 20, D-8341 Johanniskirchen, Fed. Rep. of Germany

[21] Appl. No.: 490,663

[22] PCT Filed: Jun. 24, 1989

[86] PCT No.: PCT/DE89/00421

§ 371 Date: Feb. 27, 1990

§ 102(e) Date: Feb. 27, 1990

[87] PCT Pub. No.: WO90/00185

PCT Pub. Date: Jan. 11, 1990

[30] Foreign Application Priority Data

Jun. 30, 1988 [DE] Fed. Rep. of Germany ....... 3822141

[51] Int. Cl.$^5$ .............................................. B05D 7/24
[52] U.S. Cl. .............................................. 427/2; 63/2; 106/287.14; 106/287.16; 427/387; 427/388.2; 428/447; 428/450; 523/105
[58] Field of Search ............. 427/2, 387, 388.1, 388.2, 427/409; 428/447, 450, 626, 631; 523/105; 106/287.16, 287.14; 63/2

[56] References Cited

U.S. PATENT DOCUMENTS

| 3,187,752 | 6/1965 | Glick | 427/2 |
| 4,495,254 | 1/1985 | Hoffman | 428/471 |

FOREIGN PATENT DOCUMENTS

| 3407093 | 8/1985 | Fed. Rep. of Germany | 427/387 |
| 2443484 | 7/1980 | France . | |
| 59-43070 | 3/1984 | Japan | 427/387 |
| 1264228 | 2/1972 | United Kingdom | 427/387 |
| 1447254 | 8/1976 | United Kingdom | 523/105 |
| 2067582 | 7/1981 | United Kingdom | 428/447 |

OTHER PUBLICATIONS

"Clear Silicone Coating Offers Adherence, Continuity", Products Finishing (Aug. 1962) pp. 44-50.

*Primary Examiner*—Shrive Beck
*Assistant Examiner*—Terry J. Owens
*Attorney, Agent, or Firm*—Nields & Lemack

[57] ABSTRACT

The use of a silicone as a coating for the surfaces, coming into direct contact with human skin, of metallic objects in order to produce metallic objects with an effective protection against allergic reactions of the body. The silicone is applied to the respective surfaces in a low-viscosity form and the coating so produced is allowed to dry in the air. The application of the silicone is best and preferably performed with a small brush or a spraying device.

1 Claim, No Drawings

USE OF A SILICONE AS A COATING FOR SURFACES OF METALLIC OBJECTS COMING INTO DIRECT CONTACT WITH THE HUMAN SKIN

BACKGROUND OF THE INVENTION (1) Field of the Invention

The invention relates to metallic objects which are in direct and continuous contact with the human skin such as fashion jewelry (earrings, arm bands, necklaces, etc.)

(2) Description of the Related Art

Metallic objects, which are in direct and continous contact with the human skin such as fashion jewelry (earrings, arm bands, necklaces etc) suffer from the defeat that the objects often cause allergic reactions on the and/or in the organism in a manner spreading out from the point of contact.

Presently there is an ever increasing number persons who react to base metals such as nickel and cobalt etc, which often make up a substantial fraction of alloys of metallic objects. The consequence of these reactions is usually in the form of itching and/or wet skin sores or at least a painful rash of the skin which greatly impairs its appearance. Sometimes the reactions may affect the organism generally and lead to disorders of various parts of the body. It is quite clear that more especially female persons suffer under such reactions not only bodily but also suffer psychic troubles owing to loss in self-confidence. If allergic reactions are to be avoided, it then necessary to substantially dispense with costume jewelry, but this may be seen from experience to be done very unwillingly, because jewelry is regarded as an expression of the personality even today. Or it is possible to provide a remedy by taking suitable measures.

Since commercially so far no effective protection against allergies has been offered, people are forced to adopt self-help measures. These measures reside in covering the surfaces of the costume jewelry, which would otherwise come into direct contact with the skin, with adhesive plaster or with nail varnish. The latter then forms a thin guard layer on the respective surfaces of the metallic costume jewelry after application and drying. The defects that are connected with the use of adhesive plaster are obvious. It is in this manner that in fact substantially only large surfaces may be covered over, and smaller surfaces as for instance the surfaces of rings, necklaces or thin arm bands may not be covered over or if they are covered, the adhesive plaster will be readily seen from the outside. If one considers that such adhesive plaster is liable to be become dirty, more especially when used for long periods of time, it will be clear that such measure does not satisfactorily solve the problem in question.

On the other hand nail varnish does not come up to expectations. In fact, nail varnish contains plasticizer. Plasticizers are necessary in order to give the nail varnish the necessary elasticity and a satisfactory adherence on the surface of the nail after the nail varnish has been applied and has dried. However, plasticizers have the disadvantage that they slowly sweat out, that is to say that they exude from the coating. The final result of this is that the coating becomes porous and not longer adheres to the metallic surface and finally flakes off. The protective function of such a coating is accordingly only slight.

A further point is that plasticizers themselves are often allergenic so that they cause corresponding reactions on the skin.

Measures which are such that they effectively protect the human skin on direct contact with the surfaces of metallic structures are just as unknown as coatings which are able to effectively protect the human skin on direct contact with the surfaces of metallic structures. There is thus a clear case that there is a substantial need for such measures or coatings.

SUMMARY OF THE INVENTION

The object of the present invention is the production of metallic objects with an effective protection against allergic reactions of the organism.

This object is attained by using a silicone as a coating for the surfaces, coming into direct contact with the human skin, of metallic objects.

It has surprisingly been found that the silicone used in accordance with the invention leads to metallic objects, which provide a long-lasting and effective protection against allergic reactions.

DESCRIPTION OF THE PREFERRED EMBODIMENTS

In accordance with the invention, the silicone is applied to the surfaces, coming into direct contact with the skin, of the metallic objects in the form of a low-viscosity preparation and the coating so produced is allowed to dry in the air. The application of the silicone may advantageously be performed using as small brush or with a spray device, the silicone flowing to form a coherent protective film on the respective surfaces. The application of the silicone coating is thus performed in a particularly simple manner while at the same time guaranteeing that the coating flow into the corners, over edges and right into convolutions of the surfaces. After drying the applied silicone coating adheres firmly on the respective surfaces and it represents a transparent and impermeable protective film.

In an article in the monograph "Principles of cosmetics for the dermatologist", by Ph. Frost and St. N. Horwitz, published by The S. V. Mosby Company, London 1982, there is a proposal on page 182 concerning the avoidance of nickel allergies, in which nickel containing metallic balls contained in the nail varnish bottle and serving to keep the nail varnish in the bottle liquid, are, in accordance with the proposal, to be covered with a plastic coating.

It is to be noted firstly in this connection that in this case the plastic is admittedly used for producing a coating on the metallic surfaces, but on the other hand this coating has a completely different purpose since it is not intended to provide protection against allergies due to metallic objects which come into direct contact with the skin and instead has the purpose of protecting nails, skin etc, which come into contact with the nickel particles which are contained in the nail varnish and result from metallic objects, which are not in direct contact with the skin.

The problems which then occur are quite different and are to be differently appraised to the problems of the present case.

In the case of the suggestion the one and only point is that the plastic serving as a coating should be resistant to the solvents used in the nail varnish and it is not a question of the plastic producing allergic reactions on the skin (as is a known phenomenon with many plastics), this simply being because the plastic does not come into contact with the skin at all. The selection criteria for the plastic are thus entirely different to the criteria applying for the plastic in the present invention.

Furthermore, the man in the art learning of this proposal, would right from the outset consider it to be useless, because it would not involve any advance from the use of nail varnish, for the same troubles occur. In order to endow the plastic coating with sufficient elasticity and adherence, a man in the art attempting put the proposal into practice, would see himself compelled to add a plasticizer to the plastic. The slow sweating out of the plasticizer from the coating would then involve the same problems as have been described above in connection with the nail varnish.

In the present invention it is an advantage that the silicone coatings very strongly adhere to the metallic surfaces, although the same do not contain any plasticizer and there is the further advantage that the plastic used for the coating is hardly allergenic.

The following example will explain the invention.

With the aid of a small brush a low-viscosity silicone coating is applied to the inner surface of an arm band and the coating is allowed to dry in the air.

The silicone used for the coating is a silicone rubber in the form of dimethylpolysiloxane with the addition of pyrogenic silicic acid as a filler and an oximosilane crosslinking agent. The density of the rubber amounted to 1.066 g/ml at 23° C. and viscosity as measured in a Brookfield rotary viscometer at 23° C. amounted to 10,000 mPa s.

The silicone rubber used is a commercially available product.

I claim:

1. A method for providing effective protection against allergic reactions of human skin to a surface of a metallic object which, in use, is in direct and continuous contact with said human skin, comprising: coating said surface with a silicone.

* * * * *